United States Patent
Ratcliffe et al.

(10) Patent No.: US 9,597,430 B2
(45) Date of Patent: Mar. 21, 2017

(54) SYNTHETIC STRUCTURE FOR SOFT TISSUE REPAIR

(75) Inventors: Anthony Ratcliffe, Del Mar, CA (US); Andreas Kern, San Diego, CA (US); Mohammad Sotoudeh, San Diego, CA (US); Fatemeh Ratcliffe, Del Mar, CA (US)

(73) Assignee: Synthasome, Inc., San Diego, CA (US)

( * ) Notice: Subject to any disclaimer, the term of this patent is extended or adjusted under 35 U.S.C. 154(b) by 817 days.

(21) Appl. No.: 12/533,473

(22) Filed: Jul. 31, 2009

(65) Prior Publication Data
US 2011/0029078 A1 Feb. 3, 2011

(51) Int. Cl.
*A61F 2/08* (2006.01)
*A61L 27/50* (2006.01)

(52) U.S. Cl.
CPC .............. *A61L 27/50* (2013.01); *A61F 2/08* (2013.01); *Y10T 29/49826* (2015.01)

(58) Field of Classification Search
USPC ...................... 623/11.11, 13.11, 13.17–13.18
See application file for complete search history.

(56) References Cited

U.S. PATENT DOCUMENTS

| | | | |
|---|---|---|---|
| 4,987,665 A | 1/1991 | Dumican et al. |
| 5,024,669 A | 6/1991 | Peterson et al. |
| 5,263,984 A | 11/1993 | Li et al. |
| 5,399,665 A | 3/1995 | Barrera et al. |
| 5,492,697 A | 2/1996 | Boyan et al. |
| 5,549,904 A | 8/1996 | Juergensen et al. |
| 5,567,435 A | 10/1996 | Hubbell et al. |
| 5,709,854 A | 1/1998 | Griffith-Cima et al. |
| 5,860,948 A | 1/1999 | Buscemi |
| 5,900,245 A | 5/1999 | Sawhney et al. |
| 5,906,934 A | 5/1999 | Grande et al. |
| 6,123,727 A | 9/2000 | Vacanti et al. |
| 6,129,761 A | 10/2000 | Hubbell |
| 6,224,893 B1 | 5/2001 | Langer et al. |
| 6,258,870 B1 | 7/2001 | Hubbell et al. |
| 6,378,527 B1 | 4/2002 | Hungerford et al. |
| 6,458,889 B1 | 10/2002 | Trollsas et al. |

(Continued)

FOREIGN PATENT DOCUMENTS

| WO | WO 93/17669 | 9/1993 |
|---|---|---|
| WO | WO 94/25080 | 11/1994 |

(Continued)

OTHER PUBLICATIONS

International Search Report from International Application No. PCT/US2010/043881 mailed Feb. 15, 2011.

(Continued)

*Primary Examiner* — Thomas J Sweet
*Assistant Examiner* — Tiffany Shipmon
(74) *Attorney, Agent, or Firm* — Carter, DeLuca, Farrell & Schmidt, LLP

(57) ABSTRACT

Synthetic structures for soft tissue repair include a multi-layer planar fibrillar structure having layers which are intermittently secured to each other and which approximates mechanical properties comparable to those of soft tissue. In embodiments, the fibrillar structure possesses an intermittently secured edge portion secured by intermittent welds. In embodiments, the multi layer planar fibrillar structure includes a bioactive agent.

38 Claims, 3 Drawing Sheets

(56) References Cited

U.S. PATENT DOCUMENTS

| | | |
|---|---|---|
| 6,465,001 B1 | 10/2002 | Hubbell et al. |
| 6,471,993 B1 | 10/2002 | Shastri et al. |
| 6,497,726 B1 | 12/2002 | Carter et al. |
| 6,497,729 B1 | 12/2002 | Moussy et al. |
| 6,554,867 B1 | 4/2003 | Joos |
| 6,576,000 B2 | 6/2003 | Carrison |
| 6,592,623 B1 | 7/2003 | Bowlin et al. |
| 6,624,245 B2 | 9/2003 | Wallace et al. |
| 6,679,914 B1 * | 1/2004 | Gabbay ............ 623/14.12 |
| 6,719,797 B1 | 4/2004 | Ferree |
| 6,924,370 B2 | 8/2005 | Chudzik et al. |
| 7,252,685 B2 * | 8/2007 | Bindseil et al. ......... 623/16.11 |
| 2003/0212461 A1 | 11/2003 | Vadurro et al. |
| 2004/0175408 A1 | 9/2004 | Chun et al. |
| 2004/0267362 A1 | 12/2004 | Hwang et al. |
| 2005/0196377 A1 | 9/2005 | Ratcliffe et al. |
| 2006/0160734 A1 | 7/2006 | Kusanagi et al. |
| 2006/0252981 A1 | 11/2006 | Matsuda et al. |

FOREIGN PATENT DOCUMENTS

| | | | | |
|---|---|---|---|---|
| WO | WO 2006/089267 | * | 8/2006 | ............ A61F 2/08 |
| WO | WO 2008/100589 A1 | | 8/2008 | |
| WO | 2009152215 A2 | | 12/2009 | |

OTHER PUBLICATIONS

Office Action issued on Feb. 3, 2014, in corresponding European patent application No. 10740106.9.

* cited by examiner

Figure 3. Theoretical stress-strain curve for a biological tissue.

SYNTHETIC STRUCTURE FOR SOFT TISSUE REPAIR

BACKGROUND

1. Technical Field

Synthetic structures for the repair of soft tissue are described. Such structures may include, in embodiments, fibrillar structures that may be utilized to approximate the physical characteristics of soft tissue and thus may be useful as implants to promote the repair of soft tissue.

2. Background

There are currently several ways in which various types of soft tissues such as ligaments or tendons, for example, are reinforced and/or reconstructed, such as, bioprosthetic techniques or synthetic techniques. Bioprosthetic techniques include, for example: autografting, where tissue from the patient's body is used; allografting, where donor tissue from the same species is utilized; and, xenografting, in which tissue from a donor of a different species is used. Other bioprosthetic techniques for soft tissue attachment, reinforcement, and/or reconstruction have included small intestinal submucosa (SIS) or other naturally occurring extracellular matrix (ECM), and a naturally occurring ECM or ECM component. Bioprosthetic techniques may be used alone or in conjunction with synthetic devices for tissue repair.

Synthetic techniques of tissue reconstruction, reinforcement and repair do not utilize donor material. Mechanical techniques such as suturing the torn or ruptured ends of the tissue are used to restore function. Sutures may be reinforced through other synthetic non-bioabsorbable or bioabsorbable materials.

One example of a material often used in conjunction with sutures in tissue repair is a surgical mesh. Surgical meshes may be used to support and/or reinforce damaged or weakened portions of the body. Surgical meshes may also be used as a scaffold for tissue regeneration. In this regard, the mesh must be sufficiently porous to allow for growth of tissue through the mesh after implantation. The healing tissue grows through porous openings in the implanted mesh, thereby assimilating the mesh and adding structural integrity to the tissue. Surgical meshes may also be utilized in tendon repair. Tendons of the body are under continuous movement causing stress and tension or pulling in the tendon. Accordingly, surgical meshes used in tendon repair should exhibit sufficient yield and tensile strength to endure the weight and stress or strain put on the tendon. However, the mesh should also be flexible and pliable enough to move with the tendon without breaking. The mesh should also be suturable and have a high suture pullout strength to allow the implant to function properly in vivo.

Various surgical meshes attempt to provide strength by knitting, weaving, braiding, or otherwise forming a plurality of yarns into a support trellis. These meshes may be produced with monofilament or multifilament yarns made of materials such as polypropylene and polyester. Surgical mesh formed of monofilament yarn provides satisfactory reinforcement ability, but is often stiff and has limited pliability.

SUMMARY

The present disclosure provides an implant, which includes a multi-layer planar fibrillar structure wherein the layers of the fibrillar structure are intermittently secured to each other on at least one edge portion. The multi-layer planar fibrillar structure of the implant may approximate mechanical properties of soft tissue. The multi-layer planar fibrillar structure may include two layers. The edge portion of the implant may be intermittently secured by intermittent ultrasonic welds. In embodiments, two opposing edge portions of the multi-layer planar fibrillar structure are intermittently secured. In embodiments, the multi-layer planar fibrillar structure includes two unsecured opposing edge portions.

In embodiments, the multi-layer planar fibrillar structure of the implant is bioabsorbable. In embodiments, the bioabsorbable multi-layer planar fibrillar structure is fabricated from glycolide, lactide, trimethylene carbonate, dioxanone, caprolactone, alkylene oxides, ortho esters, collagen, hyaluronic acids, alginates, and/or combinations thereof.

In embodiments, the multi-layer planar fibrillar structure of the implant is non-bioabsorbable. The non-bioabsorbable multi-layer planar fibrillar structure may be fabricated from polypropylene, polyethylene, polyamide, polyalkylene therephalate, polyvinylidene fluoride, polytetrafluoroethylene and/or combinations thereof.

In embodiments, the multi-layer planar fibrillar structure is adapted to approximate the mechanical properties of a human tendon and/or a human ligament. In embodiments, multi-layer planar fibrillar structure is has a stiffness of from about 10 to about 500 Newtons per millimeter. In embodiments, the multi-layer planar fibrillar structure has a tensile strength of from about 20 to about 2000 Newtons. In embodiments, the multi-layer planar fibrillar structure is has a failure strain at from about 105% to about 170% of its original length.

In embodiments, the multi-layer planar fibrillar structure has from about 10 to about 200, e.g. about 150, warp fibers per inch. At least one layer of the multi-layer planar fibrillar structure may be felt, knitted, woven, or non-woven.

The multi-layer planar fibrillar structure may include least one fiber having a diameter from about 10 microns to about 200 microns or multi-layer planar fibrillar structure may include at least two fibers of different diameters.

The multi-layer planar fibrillar structure may have a suture pullout strength from about 80 N to about 1200 N per centimeter of structure width. In embodiments, the suture pullout strength may be, e.g., about 350 N per centimeter of structure width.

The multi-layer planar fibrillar structure may include a bioactive agent. In embodiments, the bioactive agent is within at least one secured edge portion. In embodiments, the implant includes three layers wherein the middle layer contains a bioactive agent. The middle layer may be secured between the layers of the multi-layer planar fibrillar structure or the middle layer may not be secured. In embodiments, the middle layer is non-woven, woven, knitted, hydrogel, or combinations of these. In embodiments, the middle layer is felt. In embodiments the bioactive agent includes platelet-rich plasma, bone marrow, growth factor and combinations of these.

The present disclosure also provides an implant having a multi-layer planar fibrillar structure having a first woven layer; a felt middle layer; and a second woven layer. The first and second woven layers are intermittently secured to each other on at least one edge portion. In embodiments, the middle layer includes a bioactive agent selected from platelet-rich plasma, bone marrow, growth factor and combinations thereof.

The present disclosure further includes a method of treating soft tissue. The method includes providing an implant comprising a multi-layer planar fibrillar structure wherein the layers of said fibrillar structure are intermittently secured on at least one edge portion and affixing the fibrillar structure to the soft tissue or portions thereof. The soft tissue may be a tendon or a ligament. In embodiments, the fibrillar structure is adapted to approximate mechanical properties of a human tendon or a human ligament.

The present disclosure also includes a method of replacing soft tissue including providing an implant comprising a multi-layer planar fibrillar structure wherein the layers of said fibrillar structure are intermittently secured on at least one edge portion and affixing the fibrillar structure to a member to muscle, bone, ligament, tendon, and/or portions thereof. The fibrillar structure may approximate the mechanical properties of a tendon or a ligament. In embodiments, the tendon or ligament is a human tendon or a human ligament.

The present disclosure also includes a method of manufacturing an implant including providing a first planar fibrillar structure having at least one edge portion, providing a second planar fibrillar structure having at least one edge portion; and intermittently securing edge portions of the first planar fibrillar structure to the edge portion of the second planar fibrillar structure to form an implant having at least one intermittently secured edge portion. The intermittently securing may be intermittently welding. The method further includes providing a third planar fibrillar structure, which includes a bioactive agent and positioning it between the first and second planar fibrillar structures. The third planar structure may be felt and the bioactive agent may be platelet rich plasma, bone marrow, growth factors and combinations of these.

DETAILED DESCRIPTION OF PREFERRED EMBODIMENTS

Figure 1:
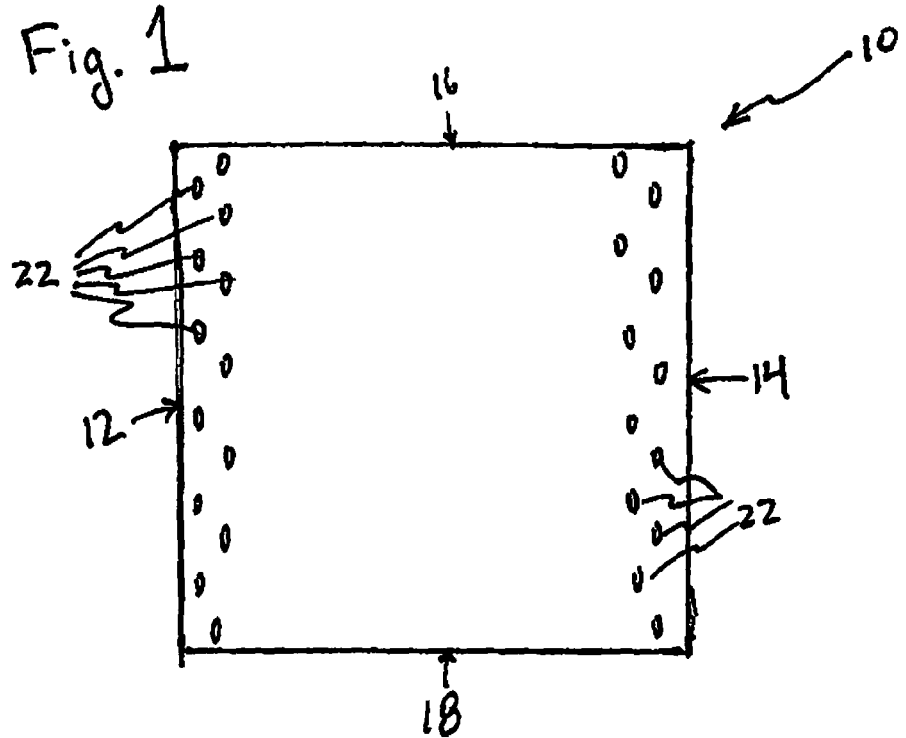
FIG. 1 is a top view of one embodiment of an implant of the present disclosure having opposing parallel edge portions intermittently secured.

A synthetic implant for soft tissue repair may include a multi-layer planar fibrillar structure that is adapted to approximate mechanical properties of soft tissue. In embodiments, the fibrillar structure may be a multi-layer planar structure which is adapted to approximate the mechanical properties of a tendon and/or ligament. In embodiments, the multi-layer planar fibrillar structure is adapted to approximate the mechanical properties of a human ligament and/or human tendon.

In embodiments, the formation of an intermittently secured edge portion of the multi-layer planar fibrillar structure provides a fibrillar structure of the present disclosure with enhanced strength at the point of attachment and may minimize the chance that the fibrillar structure of the present disclosure may become detached from the sutures or similar means utilized to affix a fibrillar structure of the present disclosure to tissue. In addition, intermittently secured edge portions, in contrast to a continuous length of attachment, allow the fibrillar structure to be more flexible, especially in the edge portion.

The mechanical properties of soft tissue and/or the multi-layer planar fibrillar structures in accordance with the present disclosure may be determined by any technique within the purview of those skilled in the art. For example, mechanical properties of soft tissue and/or the fibrillar structures can be determined by placing a sample in a spring loaded clamp attached to the mechanical testing device and subjecting the sample to constant rate extension (5 mm/sec) while measuring load and displacement and recording the resulting strain-stress curve. In embodiments, the multi-layer planar fibrillar structure may exhibit a stiffness approximating the stiffness of soft tissue. In embodiments, a suitable stiffness may be from about 10 to about 500 Newtons per millimeter (N/mm), and suitable tensile strength may be from about 20 to about 2000 Newtons. In embodiments, the stiffness of the polymeric fibrillar structure will be from about 20 to about 80 N/mm. In embodiments, the fibrillar structure may exhibit a failure strain at from about 105% to about 160% of its original length.

The fibrillar structure may be prepared using any method within the purview of those skilled in the art. For example, the fibrillar structure may be woven. It is also contemplated that the fibrillar structure could be a non-woven structure, provided that it possesses suitable mechanical properties, for example, the stiffness, tensile strength, and/or failure strain described above. In embodiments, each layer of the fibrillar structure may be woven and include from about 10 to about 200 warp fibers per inch, e.g., about 180 fibers per inch, in embodiments from about 30 to about 100 warp fibers per inch. In embodiments, from about 50 to about 75 warp fibers per inch.

The fibrillar structure may be prepared from fibers having a diameter of from about 10 microns to about 1.0 mm; in embodiments from about 15 microns to about 200 microns; in embodiments from about 20 microns to about 50 microns. Each layer of the fibrillar structure may be prepared from monofilaments, traditional multifilament yarns, or bi-component multifilament yarns. In embodiments each layer of the fibrillar structure may be prepared from multiple fibers of at least two different diameters.

The multi-layer planar fibrillar structure can be made from any biocompatible polymeric material capable of providing suitable mechanical properties. The biocompatible material may be bioabsorbable, non-bioabsorbable, or a combination of bioabsorbable and non-bioabsorbable. Suitable absorbable materials include, but are not limited to, glycolide, lactide, trimethylene carbonate, dioxanone, caprolactone, alkylene oxides, ortho esters, polymers and copolymers thereof, collagen, hyaluronic acids, alginates, and combinations thereof. Suitable non-absorbable materials include, but are not limited to, polypropylene, polyethylene, polyamide, polyalkylene therephalate (such as polyethylene therephalate, polybutylene therephalate, and the like), polyvinylidene fluoride, polytetrafluoroethylene, and blends and copolymers thereof.

In embodiments the each layer of the fibrillar structure may have the same characteristics, i.e., number of fibers, fiber diameter, absorbability, and the like. In embodiments, the characteristics of the layers of the fibrillar structure may be different.

The layers of the multi-layer planar fibrillar structure are intermittently secured. "Intermittently secured" is intended to mean a series of discrete points of attachment. Methods of intermittently securing the fibrillar structure may include, for example, intermittent ultrasonic welding, intermittent stitching, intermittent gluing, or intermittent welding. Securing the layers intermittently allows for secure attachment between layers of the fibrillar structure while simultaneously providing flexibility in the secured edge portion similar to that in the unsecured edge portions. The discrete points of attachment may be arranged linearly in one or more lines, staggered or in any other pattern.

In embodiments, the layers of the multi-layer planar fibrillar structure may be manufactured by providing a first and second fibrillar structure each having at least one edge portion and intermittently securing the edge portion of the first planar fibrillar structure to the edge portion of the second planar fibrillar structure to form an implant having at least one intermittently secured edge. For example, the planar fibrillar structures may be sonically welded on opposite edge portions using an ultrasonic welder. As another example, the planar fibrillar structures may be intermittently secured by intermittent stitching.

As used herein the term "edge portion" includes the outside edge of the fibrillar structure to an area recessed therefrom by approximately 10% of the size of the fibrillar structure.

The dimensions of the multi-layer planar fibrillar structure may be any suitable dimensions. The dimensions of the each layer of the multi-layer planar fibrillar structure can vary within those ranges conventionally used for a specific application and delivery device. For example, such ranges include dimensions of about 1 centimeter by about 1 centimeter, to about 15 centimeters by about 15 centimeters. Although described herein as square shaped, the planar fibrillar structure may be any geometric shape, for example, round, polygonal, square, or oblong. In embodiments, a thin mesh may be formed having a thickness from about 0.05 millimeters to about 1.0 millimeters, in embodiments from about 0.1 millimeters to about 0.75 millimeters. The present multi-layer planar fibrillar structures may advantageously be dimensioned to it to be rolled or otherwise folded so as to fit within a cannula having a small diameter to allow arthroscopic or laparoscopic implantation. In embodiments, the fibrillar structures in accordance with the present disclosure may define openings on the order of from about 0.5 mm to about 2 mm, in embodiments from about 0.7 mm to about 1.3 mm.

In embodiments, the implant of the present disclosure exhibits a suture pullout strength from about 80 N to about 1200 N per centimeter of structure width. In embodiments, the suture pullout strength may be, e.g., about 350 N per centimeter of structure width. As used herein "suture pullout strength" means the maximum force required to pull simple loops of sutures through the ends of the multi-layer planar fibrillar structure.

In embodiments, the multi-layer planar fibrillar structure of the present disclosure may have two layers. In embodiments, the multi-layer planar fibrillar structure may have three or four or more layers. The layers of the multi-layer planar fibrillar structure of the present disclosure may include at least one edge portion intermittently secured. In embodiments, the intermittently secured edge portion may be referred to as a "secured edge portion." The intermittently secured edge portion of the multi-layer planar fibrillar structure may be formed by ultrasonic welding. In embodiments, all of the edge portions of a multi-layer planar fibrillar structure may be intermittently secured. In embodiments edge portions of the multi-layer planar fibrillar structure may be intermittently secured at more than one edge portion.

A two layer square embodiment of the multi-layer plannar fibrillar structure of the present disclosure is depicted, for example, in FIG. 1. The embodiment of FIG. 1 includes a multi-layer planar fibrillar structure 10 of the present disclosure having two layers 24 and 26 (layer 24 not shown). These layers 24, 26 (layer 24 not shown) include secured edge portions 12 and 14, and unsecured edge portions 16 and 18. As depicted in FIG. 1, secured edge portions 12, 14, are intermittently welded along rows 20 and 22 at numerous points. In embodiments, not shown, multiple rows of intermittent welding may be utilized to form the secured edge portions 12, 14 of the multi-layer planar fibrillar structure 10. In embodiments, not shown, one or more rows of intermittent welding may secure edge portions 16 and 18, of the multi-layer planar fibrillar structure.

Figure 2:
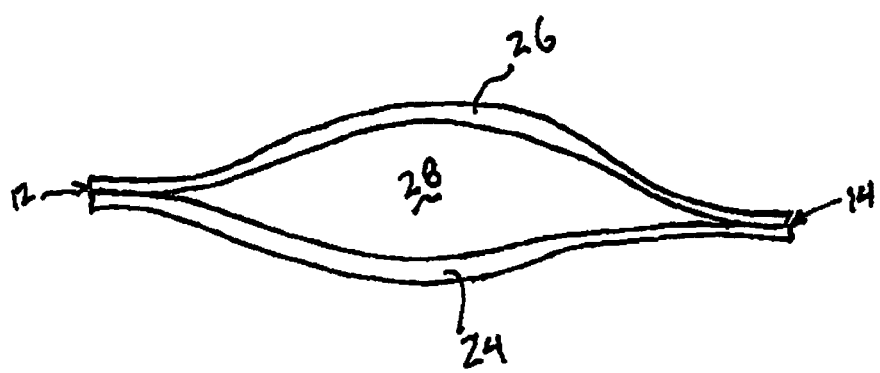
FIG. 2 is a side view of one embodiment of an implant of the present disclosure having a through-hole between unsecured edge portions.
Figure 3:
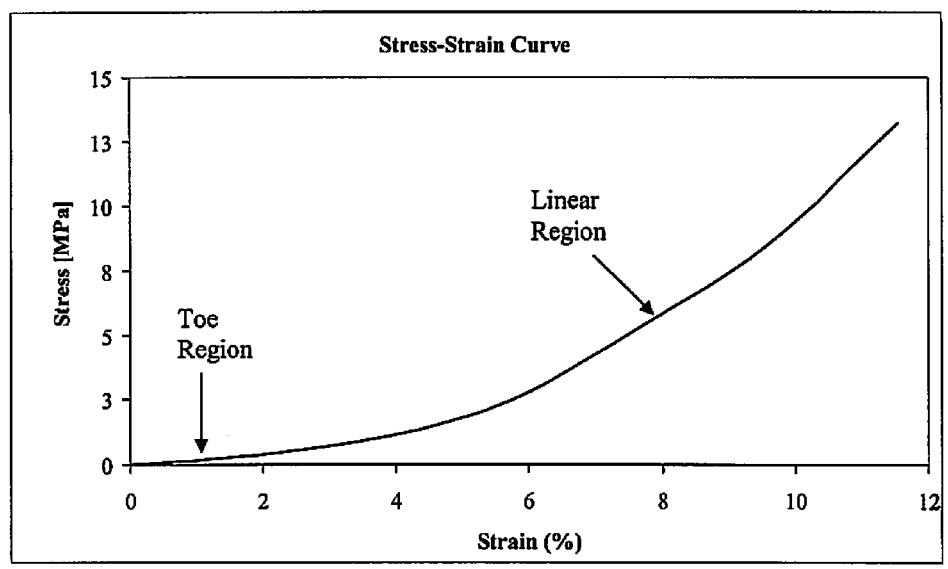
FIG. 3 shows a theoretical strain-stress curve for a biological tissue.

In embodiments, two secured edge portions of the multi-layer planar fibrillar structure may create a through-hole or "tunnel" between the unsecured edge portions. The secured edge portions then form the sides of the tunnel. FIG. 2, shows a side view of the multi-planar fibrillar structure of FIG. 1. The layers 24, 26 are separated along unsecured edge portions 18 and 16 (edge portion 16 not shown). Edge portions 12 and 14 are secured by intermittent welding 20 and 22 respectively, to form through-hole 28.

In use, the fibrillar structure may be attached to tissue utilizing any method within the purview of those skilled in the art, including the use of fasteners such as, for example, staples, barbs, sutures, tacks, adhesives, combinations thereof, and the like. Returning to FIG. 1, in embodiments, secured edge portion 12 of fibrillar structure 10 may be affixed to tissue by placing a line of sutures along welded row 20 thereby attaching edge portion 12 of fibrillar structure 10 to tissue; similarly, secured edge portion 14 of fibrillar structure 10 may be affixed to tissue by placing a line of sutures along welded row 22 thereby attaching edge portion 14 of fibrillar structure 10 to tissue.

It is further contemplated that a bioactive agent may be applied to one or more layers of the fibrillar structure. The term "bioactive agent", as used herein, is used in its broadest sense and includes any substance or mixture of substances that have clinical use. Bioactive agents may or may not have pharmacological activity, e.g., as a dye, or fragrance. Alternatively, bioactive agents may provide a therapeutic or prophylactic effect. For example, bioactive agents may affect or participate in tissue growth, cell growth, cell differentiation, and the like, and may also be able to invoke a biological action such as an immune response or play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent with a fibrillar structure of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent with a fibrillar structure of the present disclosure.

Other bioactive agents which may be included as a bioactive agent with a fibrillar structure of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included with a fibrillar structure of the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, platelet-rich plasma, bone marrow, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; extracellular matrix molecules such as fibronectin and laminin; hyaluronic acid; collagens; glycosaminoglycans; morphogens; chemoattractants; growth factors (e.g., nerve growth factor, insulin-like growth factor, EGF, FGF, PDGF and VEGF); protein inhibitors, protein antagonists, and protein agonists; nucleic acids, such as antisense molecules, DNA and RNA; oligonucleotides; polynucleotides; and ribozymes.

The bioactive materials may be applied to the fibrillar structure using any technique within the purview of those skilled in the art. For example, the bioactive agent may be applied to the fibrillar structure of the present disclosure in any suitable form of matter, e.g., films, powders, liquids, gels and the like. In embodiments, a solution of the bioactive agent in a suitable solvent may be prepared and the solvent driven off to leave the bioactive material deposited on the fibrillar structure. A further example is a bioactive agent that may be crosslinked around the fibrillar structure so as to embed one or more layers of the fibrillar structure within the bioactive agent.

Anti-adhesive agents may be used to prevent adhesions from forming between the fibrillar structures of the present disclosure and the surrounding tissues. Some examples of these agents include, but are not limited to poly(vinyl pyrrolidone), carboxymethyl cellulose, hyaluronic acid, polyethylene oxide, poly vinyl alcohols and combinations thereof.

Where a secured edge portion of the fibrillar structure is formed, a bioactive material may also be placed between the layers of the fibrillar structure prior to intermittently securing. In this manner, bioactive agents may be released at the site of attachment of the fibrillar structure, in embodiments wherein the defect itself being treated, thereby enhancing healing of the defect.

In embodiments, the bioactive material may be placed in a tube structure which, in turn, is placed between the layers of the multi-layer planar fibrillar structure. Any biocompatible material within the purview of those skilled in the art may be utilized to form a tube within which a bioactive material may be placed. Alternatively, the bioactive material itself may be tube shaped.

In embodiments, a multi-layer planar fibrillar structure includes one or more middle layers incorporating a bioactive agent. In embodiments, the one or more middle layers may be secured to adjacently disposed layers. In embodiments, the one or more middle layers may be intermittently secured to adjacently disposed layers. In embodiments, the one or more middle layers may be unsecured to adjacently disposed layers.

Figure 4:
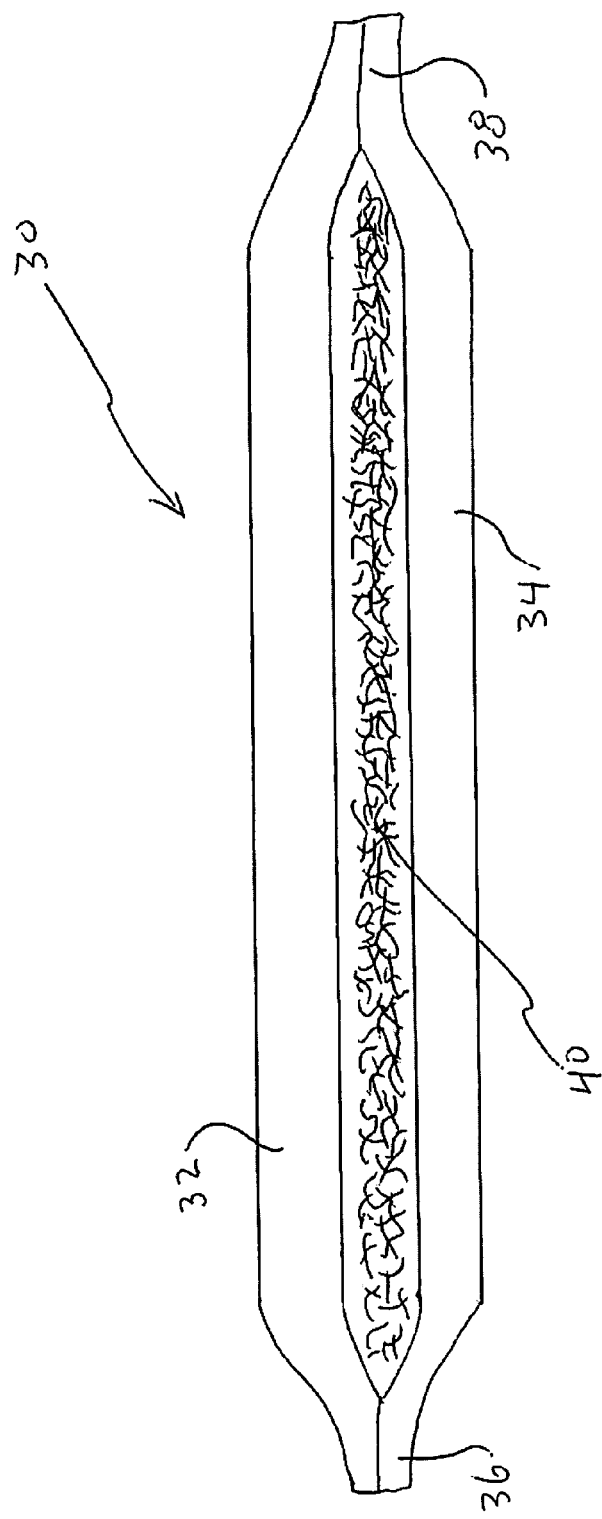
FIG. 4 is a side view of one embodiment of an implant of the present disclosure having three layers.

A three-layer multi-layer planar fibrillar structure of the present disclosure is depicted, for example, in FIG. 4. The three-layer embodiment 30 includes two fibrillar layers 32 and 34 that include intermittently secured edge portions 36 and 38. The middle layer 40 includes a bioactive agent, such as are described above. In embodiments, the bioactive agent in the middle layer 40 is bone marrow. In embodiments, the bioactive agent in the middle layer 40 is platelet-rich plasma. In embodiments, the bioactive agent may be a combination of platelet rich plasma and bone marrow. The middle layer 40 may be of the same or different material than the two fibrillar layers 32, 34. For example, the structure of the middle layer 40 may be non-woven, woven, knit, a hydrogel, or combinations thereof. In embodiments, the middle layer is felt. In embodiments, the middle layer 40 is intermittently secured to the fibrillar layers 32, 34. In embodiments, the middle layer 40 rests between the fibrillar layers 32, 34 but is not secured therein.

Each of the two or more layers of the multi-layer planar fibrillar structure may have the same or different mechanical properties, provided that the combination of the two or more layers approximates mechanical properties of soft tissue. As used herein, "approximates mechanical properties of soft tissue" means close to or exactly the same as at least one property of the soft tissue, which is intended to be treated or replaced. Such properties include but are not limited to stiffness, modulus of elasticity, tensile strength, and the like. In embodiments, each of the two or more layers may have the same or different bioabsorbability properties. In embodiments, each of the two or more layers may optionally have the same or different bioactive materials applied thereto.

The fibrillar structure may be packaged and sterilized in accordance with any of the techniques within the purview of those skilled in the art. The package in which the implant or plurality of implants are maintained can take a variety of forms within the purview of those skilled in the art. The packaging material itself can be bacteria and fluid or vapor impermeable, such as a film, sheet, or tube made of polyethylene, polypropylene, poly(vinylchloride), poly(ethylene terephthalate), and the like. Seams, joints, seals, and the like may be formed in such packaging by conventional techniques, such as, for example, heat sealing and adhesive bonding. Examples of heat sealing include sealing through the use of heated rollers, sealing through use of heated bars, radio frequency sealing, and ultrasonic sealing. Peelable seals based on pressure sensitive adhesives may also be used.

The fibrillar structures described herein can be used to treat, i.e., to repair, support, and/or reconstruct soft tissue, such as ligaments and tendons. In embodiments, the fibrillar structures may rapidly restore mechanical functionality to the soft tissue. In embodiments, the fibrillar structure may be used to replace soft tissue. Mechanical functionality of a human ligament or human tendon may include a stiffness, for example, from about 10 to about 500 Newtons per millimeter (N/mm). Mechanical functionality of a human ligament or human tendon may include, for example, a tensile strength from about 20 to about 2000 Newtons.

In embodiments, a single layer fibrillar structure is contemplated. One such single layer embodiment includes an edge portion having intermittently spaced ultrasonic welds to prevent the edge portion of the single layer fibrillar structure from unraveling. In other single layer embodiments one or more edges of the single layer fibrillar structure is folded over to create an edge portion, and the folded-over edge portion is intermittently secured as described above. The materials and characteristics for these single layer embodiments are the same as described above for the multi-layer embodiments.

The fibrillar structure may be implanted using conventional surgical or laparoscopic/arthroscopic techniques. The fibrillar structure may be affixed to the soft tissue or to bone adjacent to or associated with the soft tissue to be repaired. In embodiments, the fibrillar structure may be affixed to muscle, bone, ligament, tendon, or fragments thereof. Affixing the fibrillar structure can be achieved using techniques within the purview of those skilled in the art using, fasteners, with or without the use of anchors, pledgets, etc.

The present fibrillar structure may be used alone or in combination with other tissue repair products within the purview of those skilled in the art. Suitable tissue repair products that may be used in combination with the present fibrillar structures include, for example, RESTORE® a small intestine submucosa (SIS) biologic graft material that is commercially available from Depuy Orthopedics Inc., Warsaw Ind.; GRAFTJACKET®, an acellular dermal tissue matrix commercially available from Wright Medical Technology, Inc., Arlington, Tenn.; CUFFPATCH™ Type I porcine collagen material from Biomet Sports Medicine, Inc/Arthrotek (Warsaw, Ind.); TISSUEMEND® acellular collagen membrane materials from Stryker (Kalamazoo, Mich.); and ENCUFF® a cross-linked pericardium xenograft that has been subjected to an anti-calcification process commercially available from Selhigh, Inc., Union N.J. Other tissue repair products suitable for use in connection with the present fibrillar structures will be apparent to those skilled in the art. The other tissue repair product can be separate from or attached to the fibrillar structure.

In order that those skilled in the art may be better able to practice the compositions and methods described herein, the following examples are given as an illustration of the preparation of the present compositions and methods. It should be noted that the fibrillar structure is not limited to the specific details embodied in the examples.

Examples

Ultrasonic Welding Method of Multi-Layer Planar Fibrillar Structure Formation

A multi-layer planar fibrillar structure was intermittently sonically welded on two opposite edge portions. The ultrasonic welder used included an actuator and a power supply. The actuator was a Branson model #: 921AES with a 920M Power Supply Settings for the power supply and actuator are in Table 1 below.

TABLE 1

| Part/Setting | Example 1 | Example 2 | Example 3 |
| --- | --- | --- | --- |
| Pressure (PSI) | 70 | 70 | 70 |
| Welding Time (s) | 65 | 280 | 350 |
| Hold Time (s) | 1 | 1 | 1 |
| Trigger Force (lb) | 5 | 9 | 10 |
| Energy (+) limit | 75 | N/A | N/A |
| Energy (−) limit | 60 | N/A | N/A |

The resulting multi-layer planar fibrillar structure of the disclosure is represented in FIG. 1.

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

What is claimed is:

1. An implant comprising: a multi-layer planar fibrillar structure wherein the layers of said fibrillar structure are intermittently secured to each other by a series of discrete points of attachment to provide a discontinuous length of attachment on at least one edge portion.

2. The implant of claim 1, wherein the multi-layer planar fibrillar structure approximates mechanical properties of soft tissue.

3. The implant of claim 2, wherein the multi-layer planar fibrillar structure is adapted to approximate the mechanical properties of soft tissue selected from the group consisting of a human tendon and a human ligament.

4. The implant of claim 3, wherein the multi-layer planar fibrillar structure exhibits a stiffness of from about 10 to about 500 Newtons per millimeter.

5. The implant of claim 3, wherein the multi-layer planar fibrillar structure exhibits a tensile strength of from about 20 to about 2000 Newtons.

6. The implant of claim 3, wherein the multi-layer planar fibrillar structure exhibits a failure strain at from about 105% to about 160% of its original length.

7. The implant of claim 2, wherein the multi-layer planar fibrillar structure exhibits a suture pullout strength of about 180 N per centimeter of multi-layer planar fibrillar structure width.

8. The implant of claim 1, wherein the multi-layer planar fibrillar structure comprises two layers.

9. The implant of claim 1, wherein said edge portion is intermittently secured by intermittent ultrasonic welds.

10. The implant of claim 1, wherein two opposing edge portions are intermittently secured.

11. The implant of claim 1, wherein the multi-layer planar implant further comprises two unsecured opposing edge portions.

12. The implant of claim 11, wherein two secured edge portions form a throughhole between the unsecured edge portions.

13. The implant of claim 1, wherein the multi-layer planar fibrillar structure is bioabsorbable.

14. The implant of claim 13, wherein the multi-layer planar fibrillar structure is fabricated from at least a member selected from the group consisting of glycolide, lactide, trimethylene carbonate, dioxanone, caprolactone, alkylene oxides, ortho esters, collagen, hyaluronic acids, alginates, and combinations thereof.

15. The implant of claim 1, wherein the multi-layer planar fibrillar structure is non-bioabsorbable.

16. The implant of claim 15 wherein the multi-layer planar fibrillar structure is fabricated from at least a member of the group consisting of polypropylene, polyethylene, polyamide, polyalkylene therephalate, polyvinylidene fluoride, polytetrafluoroethylene and combinations thereof.

17. The implant of claim 1, wherein at least one layer of the multi-layer planar fibrillar structure has from about 10 to about 200 warp fibers per inch.

18. The implant of claim 1, wherein at least one layer of the multi-layer planar fibrillar structure is knitted.

19. The implant of claim 1, wherein at least one layer of the multi-layer planar fibrillar structure is woven.

20. The implant of claim 1, wherein at least one layer of the multi-layer planar fibrillar structure is non-woven.

21. The implant of claim 1, wherein at least one layer of the multi-layer planar fibrillar structure is felt.

22. The implant of claim 1, wherein the multi-layer planar fibrillar structure comprises at least one fiber having a diameter from about 10 microns to about 200 microns.

23. The implant of claim 1, wherein the multi-layer planar fibrillar structure comprises at least two fibers of different diameters.

24. The implant of claim 1, wherein the planar fibrillar structure includes a bioactive agent.

25. The implant of claim 1, wherein the planar fibrillar structure includes a bioactive agent within at least one secured edge portion.

26. The implant of claim 1, further comprising a middle layer containing a bioactive agent.

27. The implant of claim 26, wherein the middle layer is intermittently secured between layers.

28. The implant of claim 26, wherein the middle layer is not secured.

29. The implant of claim 26, wherein the middle layer comprises a material selected from the group consisting of non-woven, woven, knit, hydrogel and combinations thereof.

30. The implant of claim 26, wherein the middle layer is felt.

31. The implant of claim 26, wherein the bioactive agent is selected from the group consisting of platelet-rich plasma, bone marrow, growth factor and combinations thereof.

32. The implant of claim 26 wherein the multi-layer planar fibrillar structure comprises a first woven layer;
a felt middle layer containing a bioactive agent; and a second woven layer;
wherein said first woven layer and said second woven layer are intermittently secured on at least one edge portion.

33. The implant of claim 32, wherein the felt middle layer comprises a bioactive agent selected from the group consisting of platelet-rich plasma, bone marrow, growth factor, and combinations thereof.

34. The implant of claim 32 wherein the first woven layer, the felt middle layer and the second woven layer are intermittently secured to each other.

35. The implant of claim 1, wherein the discrete points of attachment are arranged linearly in one or more lines.

36. The implant of claim 1, wherein the discrete points of attachment are arranged in a staggered pattern.

37. An implant comprising:
a planar fibrillar structure comprising a first layer defining an upper surface of the planar fibrillar structure and a second layer defining a lower surface of the planar fibrillar structure;
a flexible edge portion including intermittent points of attachment of the first layer directly to the second layer to provide a discontinuous length of attachment of the first and second layers; and
an unsecured edge portion including a throughhole therebetween.

38. A mesh comprising fibrillar layers which are intermittently secured to each other on at least one edge portion to provide a discontinuous length of attachment of the fibrillar layers and form an unsecured edge portion.

* * * * *